United States Patent [19]
Inoue et al.

[11] Patent Number: 5,114,846
[45] Date of Patent: May 19, 1992

[54] PROCESS FOR PRODUCING STREPTOVARICIN

[75] Inventors: Kaname Inoue, Kawasaki; Motohide Yamazaki, Joetsu, both of Japan; Richard W. Armentrout, La Jolla, Calif.

[73] Assignee: Shin-Etsu Bio, Inc., San Diego, Calif.

[21] Appl. No.: 601,876

[22] Filed: Oct. 23, 1990

[51] Int. Cl.$^5$ .......... C12Q 1/04; C12N 1/36; C12P 17/18

[52] U.S. Cl. .......... 435/34; 435/119; 435/180; 435/245; 435/253.5; 435/253.6; 435/886

[58] Field of Search .......... 435/34, 119, 253.6, 435/245, 253.5, 180, 886; 514/183

[56] References Cited

U.S. PATENT DOCUMENTS

| | | | |
|---|---|---|---|
| 3,116,202 | 12/1963 | Dietz et al. | 435/886 |
| 3,819,485 | 6/1974 | Nara et al. | 435/119 |
| 4,031,215 | 6/1977 | Sasaki et al. | 514/183 |

OTHER PUBLICATIONS

K. L. Rinehart Jr., et al., "Relative biological activities of individual streptovaricins and streptovaricin acetates," Biochemistry, vol. 13, No. 5, pp. 861–867 (1974).

K. Sasaki, et al., "Chemical modification of streptovaricins C," J. Antibiotics, vol. 29, No. 2, pp. 147–154 (Feb. 1976).

S. Ito, et al., "Selective killing of human T cell lymphotropic virus type I-transformed cell lines by a damavaricin $F_c$ derivative," J. Antibiotics, vol. 42, No. 5, pp. 779–787 (May 1989).

Wang, "Annuals New York Academy of Sciences", V431, 1483, pp. 313-321 (1983).

*Primary Examiner*—Herbert J. Lilling
*Attorney, Agent, or Firm*—McAulay Fisher Nissen Goldberg & Kiel

[57] ABSTRACT

A method for selecting hyper-producing strains of streptovaricin C by culturing *streptomyces spectabilis* and separating the asporogenous colonies. The asporogenous colonies are then separately cultured and tested for streptovaricin productivity. Those colonies having the highest productivity may then be easily selected.

11 Claims, 4 Drawing Sheets

PROCESS FOR PRODUCING STREPTOVARICIN

BACKGROUND OF THE INVENTION

I. Field of the Invention

This invention relates to a process for the production of streptovaricin C.

II. Description of the Prior Art

U.S. Pat. No. 3,116,202 describes streptovaricins and their production. As disclosed therein, *Streptomyces spectabilis* (NRRL2494) produces five types of streptovaricins designated as types A, B, C, D, and E. It also describes the use of streptovaricin as an antituberculosis drug. However, this product has not achieved broad use for this purpose.

Example 3 of this patent discloses the accumulation of 21 mg/l of streptovaricin in the broth assuming that the crude product was 100% pure. However, the disclosure gives no indication of the amount or ratio of streptovaricin C in the crude mixture.

More recent attempts have been made to obtain novel antibiotics by chemically modifying streptovaricin C in order to provide anti-virus and anti-cancer agents (See K. Sasaki, T. Naito, T. Satomi, and K. Onodera, *The Journal of Antibiotics*, Feb. 1976, pp.147-154). (See S. Ito, N. Yamamota, K. Nomoto, K. Sasaki, and K. Onodera, *The Journal of Antibiotics*, May 1989, pp.779-787.)

These derivatives use only streptovaricin C and thus require a method for selectively preparing streptovaricin C. In the May 1989, K. Onodera et al article, the yield of streptovaricin C, the most abundant component of the streptovaricin complex provided by the Upjohn Co. and used by the authors, was about 20%. (See pages 151-152).

In K. Rinehart et al., *Biochemistry*, Vol. 13, No. 5, 1974, pp. 861-867, the content of streptovaricin C within the mixture of streptovaricins obtained from the provider (Upjohn 11560-3), was about 10 to 20%. This suggests that the streptovaricin C content in the broth of Example 3 of U.S. Pat. No. 3,116,202, was about 2-4 mg/L. These amounts and concentrations are not sufficient for further development of streptovaricin C derivatives.

A more efficient method for separating streptovaricin C from a culture broth of a streptovaricin producing strain which produces a mixture of types A, B, C, D and E, is disclosed in Japanese applications No. 14285/1990 and 14286/1990 corresponding to U.S. patent application No. 07/601,875, filed Oct. 23, 1990. (See also H. Wang, *Annals New York Academy of Sciences*, 431, 1983, pp. 313-321.) In these methods, a publicly available streptovaricin-producing strain (ATCC 27465) is cultured in the presence of a non-ionic adsorbent and with the optional addition of fumaric acid or one of its water-soluble salts. Using these methods, it was possible to increase the amount of streptovaricin C separated from the culture broth. Even so, higher productivity of streptovaricin is needed for proper development and commercial production of this compound.

SUMMARY OF THE INVENTION

We have discovered a method for selectively producing streptovaricin C from a culture broth resulting in higher yields as well as more facile isolation of the desired product, namely, streptovaricin C. More particularly, we have discovered a method for selecting a natural mutant strain belonging to the genus *Streptomyces* which is a hyper-producer of streptovaricin C.

In accordance with the invention, we have found that streptovaricin C hyper-producing strains can be easily and quickly selected from *Streptomyces spectabilis* by culturing *Streptomyces spectabilis*, and separating those colonies which are non-spore forming (asporogenous). The selected colonies are then separately cultured and tested for streptovaricin productivity. The colony or colonies having the highest desirable streptovaricin productivity is then fermented in a nutrient broth containing a compound selected from the group consisting of fumaric acid and water-soluble salts thereof, and adsorbent polymer beads and the streptovaricin produced are recovered in the usual manner.

We have discovered that by this single selection step, i.e., the selection of the asporogenous colony, a selection of a single hyper-producer out of 6000 to 10,000 normal (non hyper-producing) colonies may be achieved.

DESCRIPTION OF THE PREFERRED EMBODIMENT

Figure 1:
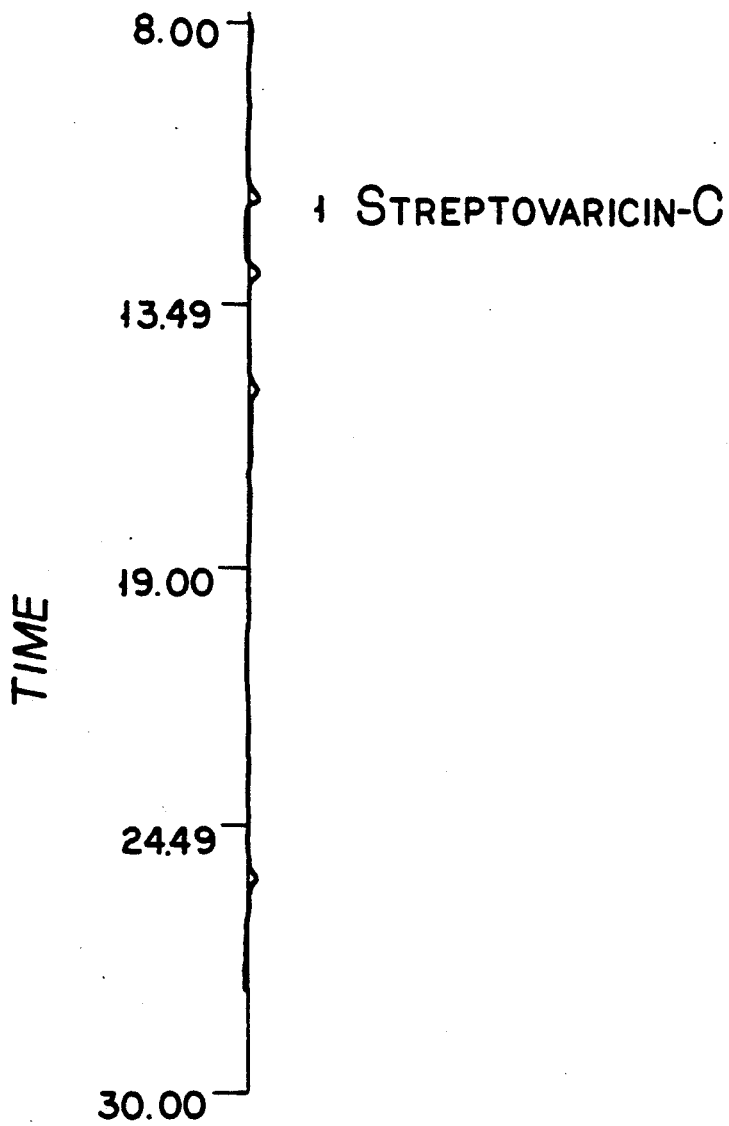
FIGS. 1, 2, 3, and 4 are high performance liquid chromatographs of product mixtures obtained with the inventive method.

*Streptomyces spectabilis* may be inoculated in a conventional manner on agar plates. Typically, these may be grown for a period of days at an appropriate temperature, e.g., 27° C. or whatever temperature is satisfactory for growth of the colonies. The colonies have a distinct appearance, being either pale yellow to white and covered with spores. However, a relatively small number of asporogenous colonies are observed. These colonies, which take approximately 4 days to grow, may turn from white/yellow to red. These colonies are separated and further cultured and tested for streptovaricin C productivity. We have found that the likelihood of obtaining a hyper-producing variant strain from such selected colonies is about 1 in 3. As used herein, a hyper-producing strain is one which produces streptovaricin C in an amount of at least about 500 mg/L. This represents a significant increase in the factor of selecting a hyperproducing strain by virtue of a single selection step.

The variant thus selected may be cultured in a conventional manner using a nutrient broth. Such nutrients may contain an assimilable carbon source, such as, starch, dextrin, glucose, sucrose, lactose, and the like; an organic nitrogen source, such as, corn steep liquor, peptone, meat extract, yeast extract, vegetable protein, casein, malt extract, dry yeast, soybean meal, and the like, and/or an inorganic nitrogen source, such as, ammonium sulfate, ammonium nitrate, potassium nitrate, and the like. Minerals may also be present, such as, calcium carbonate, potassium phosphate, magnesium sulfate, potassium chloride, sodium chloride, zinc sulfate, ferrous sulfate, manganese sulfate, cobalt chloride, ammonium molybdenate, and the like, as well as mixtures of these minerals.

The culture broth further contains fumaric acid and/or a water-soluble salt thereof. Typical salts includes sodium fumarate, potassium fumarate, potassium sodium fumarate, monosodium fumarate, monopotassium fumarate, and the like, as well as mixtures thereof.

Finally, the culture broth further contains adsorbent polymer beads which are porous and have a relatively large specific surface area.

Such polymer beads are well known in the art and described in U.S. patent application No. 07/601,875 filed concurrently hereunder, based on and claiming priority of Japanese patent application No. 14285/1990 and 14286/1990. Such polymer beads can be made by polymerizing various types of monomers, e.g., styrene, divinyl benzene, acrylic acid ester, methacrylic acid ester, and the like.

Commercially available examples of such beads are HP-10, HP-20, HP-30, HP-40, HP-50 (Mitsubishi Chemical Co.); and XAD-2, XAD-4 (Roam & Haas Co.). These beads are all copolymers of styrene and divinyl benzene. XAD-7 (Roam & Haas Co.), which is an acrylic co-polymer, may also be used.

Typically, these beads have a diameter of from 50 to 1,000 micrometers, a specific surface area in the range of from 50 to 1,000 square meters per gram and a specific pore volume in the range from about 0.2 to 1.5 ml/g. The most preferable of the above noted commercial products are HP-20, and XAD-4.

The following examples illustrate the invention:

EXAMPLE 1

Agar plates (85mm diameter) were prepared by adding 8 ml of sterile medium having the following composition Inoculum Medium to each plate:

| Inoculum Medium: | |
|---|---|
| Normal Bouillon | 18.0 g/L |
| Glucose | 6.25 |
| Yeast Extract | 2.0 |
| Agar | 15.0 |

*Streptomyces spectabilis* ATCC27465 was inoculated on agar plates to cultivate between 50 and 500 colonies on each plate. The cultures were grown on each plate for 4 days at 27° C. After this time period, all of the colonies on the plate were covered with spores, and had become a pale yellow to white color, with the exception of three colonies. These three colonies had no spores, and their color after the 4th day appeared red. The rate of appearance of these colonies was from about 1/6000 to 1/10,000.

COMPARATIVE EXAMPLE 1

A 100 ml sample of sterile medium (seed medium) having the following composition was inoculated with the normal colonies obtained from the above inoculum culture. The culture (seed culture) was incubated for 3 days at 27° C. on a rotary shaker at 175 rpm.

| Seed Medium: | |
|---|---|
| hydrolyzed casein (N-Z-Amine A) | 12.5 g/L |
| Glucose | 6.25 |
| Enzyme - decomposed extract of soybean (Soytone) | 6.25 |
| $K_2HPO_4$ | 1.56 |
| $KH_2PO_4$ | 1.56 |

The seed culture thus obtained was inoculated at a 2% concentration (v/v) in a 100 ml sterile medium having the following composition (preproduction medium). The culture (preproduction culture) was then incubated for 3 days at 27° C. on a rotary shaker at 175 rpm.

| Preproduction Medium: | |
|---|---|
| Corn dextrin | 20 g/L |
| Defatted soybean meal (Kay Soy) | 10.0 |
| Corn steep liquor | 10.0 |
| Beer yeast | 2.5 |
| KCl | 3.0 |
| $CaCO_3$ | 4.0 |

A production culture (No. 1) was prepared by inoculating 100 ml of the preproduction culture obtained above into 2L of sterile medium having the following composition (Production Medium-1) prepared in a 5L jar fermenter. The culture was fermented for 10 days at 27° C., at 300 rpm agitation, and 1 v/v/m aeration.

| Production Medium - 1: | |
|---|---|
| Glucose | 60.0 g/L |
| Soybean Meal | 20.0 |
| Beer yeast | 10.0 |
| NaCl | 6.0 |
| $CaCO_3$ | 0.5 |
| $K_2HPO_4$ | 2.5 |
| Silicon emulsion defoamer (KM75) | 2.0 |

Streptovaricin C accumulated in the broth to a concentration of 2 mg/L as determined by HPLC. FIG. 1 is the HPLC chart wherein the streptovaricin content was measured at 254 nm. The amount of Streptovaricin C was measured as being 20.7% of the various Streptovaricins.

COMPARATIVE EXAMPLE 2

A production culture (No. 2) was prepared by inoculating 100ml of the preproduction culture obtained in Comparative Example 1 in 2L of sterile medium having the following composition (production medium-2), which was prepared in a 5L jar fermenter. The culture was fermented for 10 days at 27° C., 300 rpm agitation, and 1 v/v/m aeration.

| Production Medium-2 | |
|---|---|
| Glucose | 60.0 g/L |
| Soybean Meal | 20.0 |
| Beer Yeast | 10.0 |
| NaCl | 6.0 |
| $CaCO_3$ | 0.5 |
| $K_2HPO_4$ | 2.5 |
| Monosodium Fumarate | 24.0 |
| Silicon Emulsion defoamer (KM75) | 2.0 |

Figure 2:
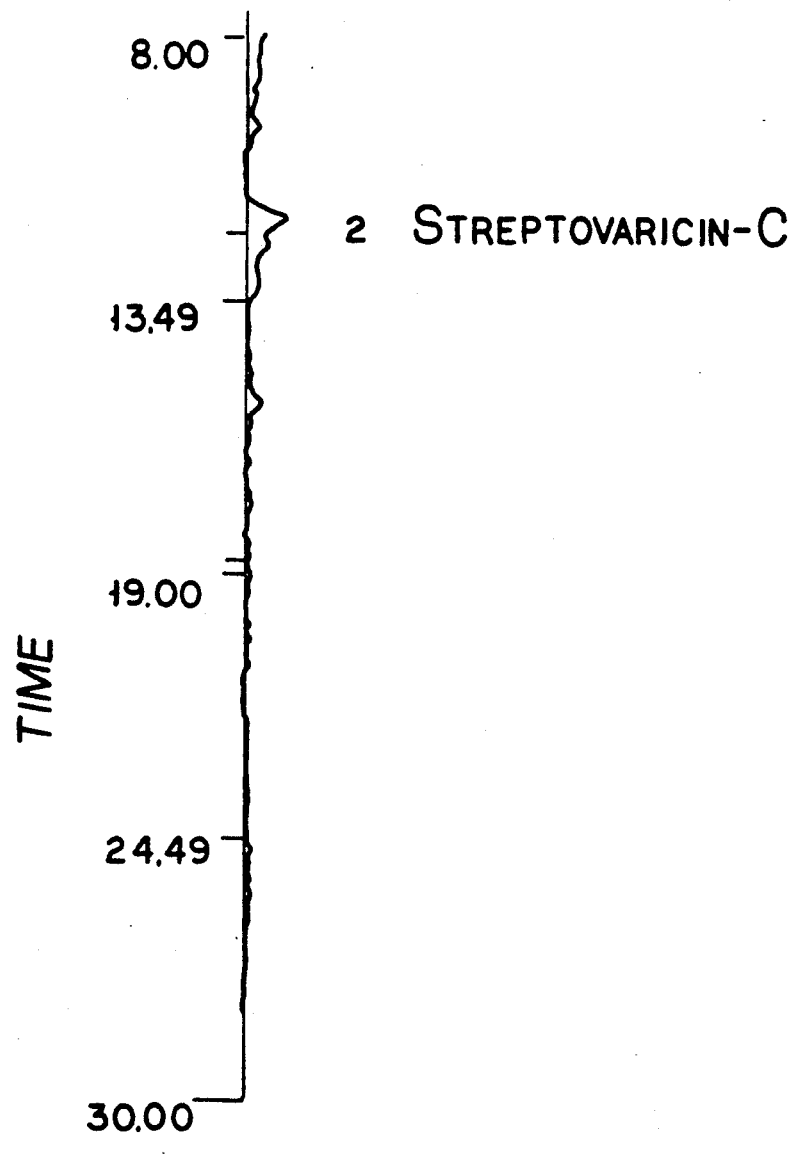

Streptovaricin C accumulated in the broth to a concentration of 8 mg/L. FIG. 2 shows that the streptovaricin C was 24.4% of the various Streptovaricins.

COMPARATIVE EXAMPLE 3

A production culture (No. 3) was prepared by inoculating 1000 ml of the preproduction culture obtained in comparative example 1 into 18L of sterile medium having the following composition (production medium-3) which was prepared in a 30L jar fermenter. The culture was fermented for 10 days at 27° C., 300 rpm agitation, and 1 v/v/m aeration.

| Production Medium-3 | |
|---|---|
| Glucose | 60.0 g/L |
| Soybean Meal | 20.0 |
| Beer Yeast | 10.0 |
| NaCl | 6.0 |
| CaCO$_3$ | 0.5 |
| K$_2$HPO$_4$ | 2.5 |
| Monosodium Fumarate | 24.0 |
| Silicon Emulsion defoamer (KM75) | 2.0 |
| Polystyrene-type adsorbent beads (DIAION HP-20; 50% solid) | 100.0 |

Figure 3:
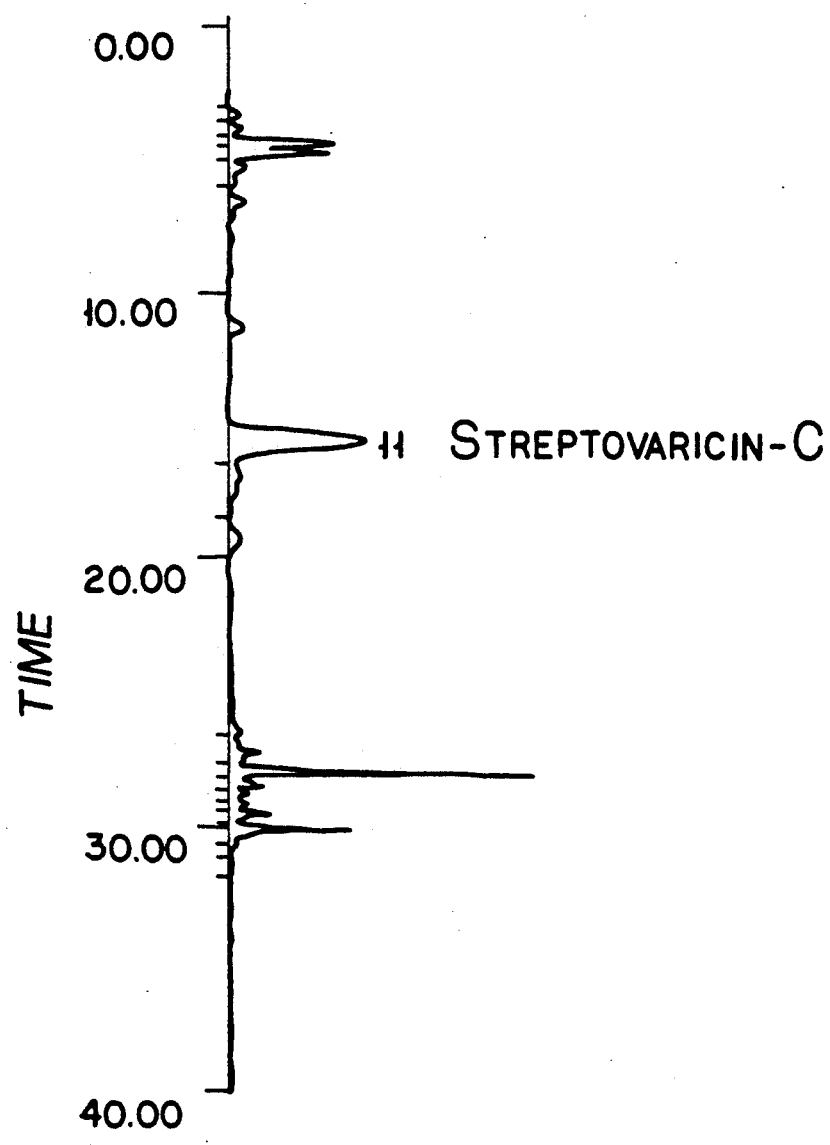

Streptovaricin C, accumulated within HP-20, was extracted and determined by HPLC to be present in a concentration of 99 mg/L. FIG. 3 is the HPLC chart showing that Streptovaricin C constitutes 29.5% of the various streptovaricins.

EXAMPLE 2

The three variants separated from example 1, were inoculated into a Seed medium, and then a Preproduction Medium. The media and incubation conditions were the same as used in Comparative Example 1. Each 1000 ml of preproduction culture obtained was then inoculated into each 18L sterile medium, the composition of which was taken from Comparative Example 3, as Production Medium-3. The cultures were then separately prepared in three 30L jar fermenters. The cultures were fermented for 14 days at 27° C., 300 rpm agitation, and 1 v/v/m aeration.

Streptovaricin C, accumulated in HP-20, was extracted and determined by HPLC. Data from two of the variants was about 100 mg/L, similar to the data found in Comparative Example 3.

Figure 4:
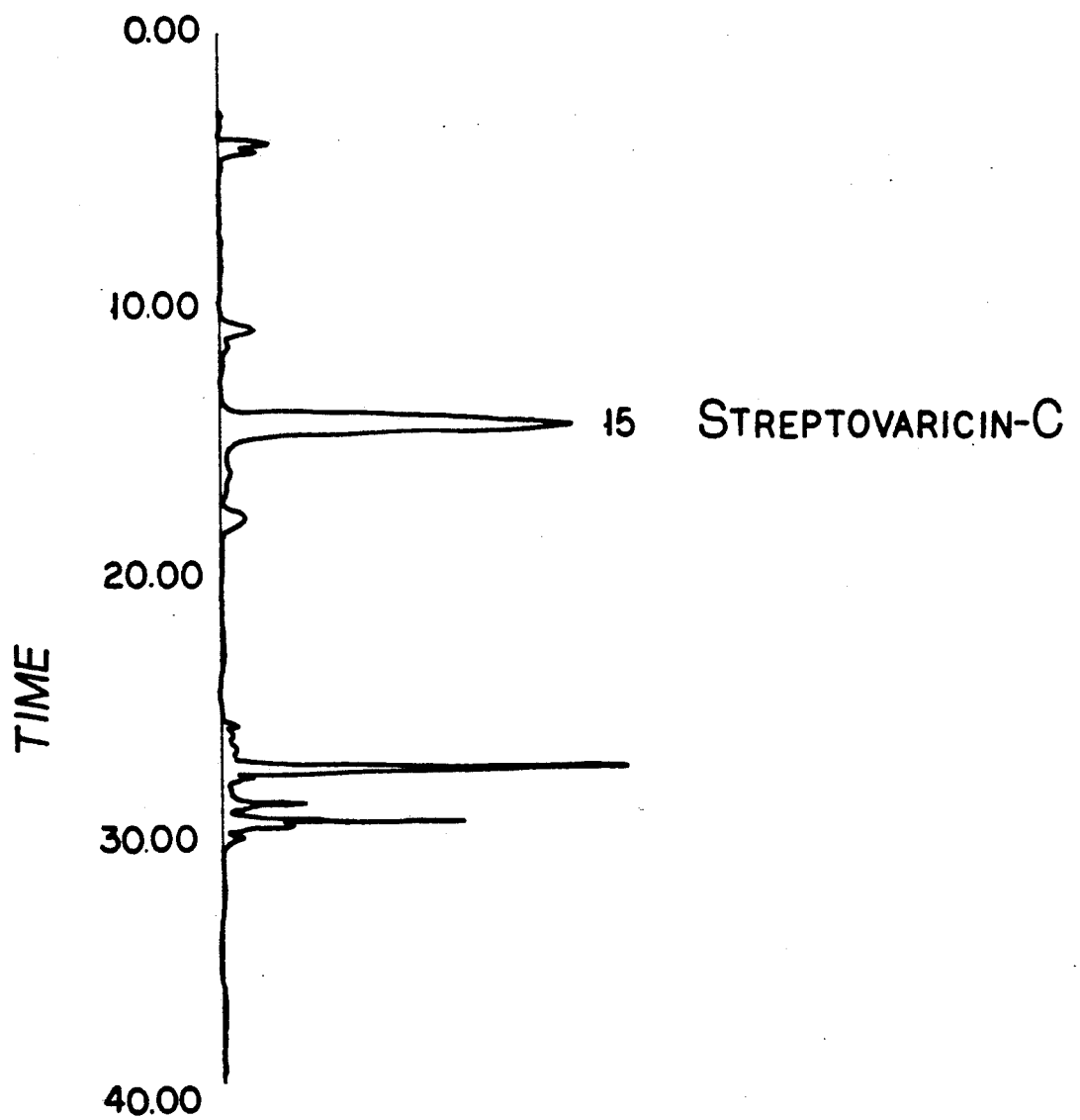

The data from the third variant was 693 mg/L, much higher than the other strains. As shown in FIG. 4, at 254 nm, the HPLC chart indicates that the amount of Streptovaricin C constitutes 47.6% of the total streptovaricins obtained. This figure was higher than any others.

This third variant has been deposited under the Budapest Treaty at the Fermentation Research Institute in Japan, 13, Higashi 1-Chrome, Tsukuba-shi, Ibaraki-ken, 305, Japan. The Deposit No. is FERM BP-3460, in the name of Shin-Etsu Bio, Inc.

EXAMPLE 3

Agar plates were prepared by adding 15 ml of the inoculum medium of Example 1 to the plates. Streptomyces spectabilis ATCC27465 was inoculated on more than 500 plates to obtain between 50,000 to 100,000 colonies. From these, 11 asporogenous colonies were obtained.

These 11 colonies were inoculated to Seed Medium and the preproduction medium in accordance with procedure and media described in Comparative Example 1. Five ml of each these preproduction cultures obtained were inoculated into 100 ml of sterile production medium-3 prepared in a 500 ml flask.

For comparison purposes, the hyperproducing strain of Example 2 is also incubated within the seed medium following by the preproduction medium. Two flasks each containing 100 ml of sterile production medium-free were inoculated separately with each 5 ml of the hyperproducer preproduction culture. The 13 flasks thus prepared were fermented for 14 days at 27° C. on a rotary shaker at 175 rpm.

Based on a comparison of the Streptovaricin C obtained from the 11 colonies, three of the 11 were hyperproducing strains equivalent to the two hyperproducer comparative strains. Accordingly, with the present method, one can easily and reproducibily select hyperproducing strains from large numbers of colonies.

What is claimed is:

1. A process for the increased production of Streptovaricin C which comprises the steps of:
   a) culturing a wild-type strain of *Streptomyces spectabilis;*
   b) growing a multiplicity of colonies from said culture;
   c) selecting those colonies which are asporogenous; and
   d) culturing a selected asporogenous colony in an aqueous nutrient broth containing an assimilable carbon source, a nitrogen source, minerals, fumaric acid or water-soluble salt of fumaric acid in the presence of absorbent polymer beads.

2. The process of claim 1 wherein the wild type strain is *Streptomyces Spectabilis ATCC27465*.

3. The process of claim 1 wherein the assimilable carbon source is selected from the group consisting of starch, dextrin, glucose, sucrose, and lactose.

4. The process of claim 1 wherein the nitrogen source is organic.

5. The process of claim 1 wherein the organic nitrogen source is selected from the group consisting of corn steep liquor, peptone, meat extract, yeast extract, vegetable protein, casein, malt extract, dry yeast, and soybean meal.

6. The process of claim 1 wherein the nitrogen source is inorganic.

7. The process of claim 6 wherein the inorganic nitrogen source is selected from the group consisting of ammonium sulfate, ammonium nitrate, and potassium nitrate.

8. The process of claim 1 wherein the mineral is selected from the group consisting of calcium carbonate, potassium phosphate, magnesium sulfate, potassium chloride, sodium chloride, zinc sulfate, ferrous sulfate, manganese sulfate, cobalt chloride, ammonium molybdenate, and mixtures thereof.

9. The process of claim 1 wherein said water-soluble salt is selected from the group consisting of sodium fumarate, potassium fumarate, potassium sodium fumarate, monosodium fumarate, monopotassium fumarate, and mixtures thereof.

10. The process of claim 1 wherein said polymer beads are made by polymerizing a monomer selected from the group consisting of styrene, divinyl benzene, acrylic acid ester, methacrylic acid ester, and combinations thereof.

11. The process of claim 1 wherein the hyperproducing strain can produce more than about 500mg/L of Streptovaricin C.

* * * * *